United States Patent [19]

Yin et al.

[11] Patent Number: 5,658,446

[45] Date of Patent: Aug. 19, 1997

[54] PREPARATIVE CAPILLARY ELECTROPHORESIS WITH WIDE-BORE CAPILLARY

[75] Inventors: Hongfeng Yin, Cupertino; Douglass McManigill, Palo Alto; Catherine A. Keely-Templin, Los Altos; Robert R. Holloway, Montara, all of Calif.

[73] Assignee: Hewlett-Packard Company, Palo Alto, Calif.

[21] Appl. No.: 688,351

[22] Filed: Jul. 30, 1996

Related U.S. Application Data

[60] Provisional application No. 60/010,396, Jan. 22, 1996.
[51] Int. Cl.[6] .................. G01N 27/26; G01N 27/447
[52] U.S. Cl. ........................... 204/451; 204/601
[58] Field of Search ................. 204/601, 602, 204/603, 604, 605, 451, 452, 453, 454, 455

[56] References Cited

U.S. PATENT DOCUMENTS

| 5,061,361 | 10/1991 | Gordon | 204/452 |
|---|---|---|---|
| 5,092,973 | 3/1992 | Zare et al. | 204/452 |
| 5,324,413 | 6/1994 | Gordon | 204/603 |

OTHER PUBLICATIONS

A. Cifuentes et al, "Rectangular Capillary Electrophoresis: Study of Some Dispersive Effects" Journal of Chromatography A, 737*(1996) 243–253.

Henrik T. Rasmussen et al, "Influence of Buffer Concentration, Capillary Internal Diameter and Forced Convection on Resolution in Capillary Zone Electrophoresis" Journal of Chromatography, 516*(1990) 223–231.

Tsukagoshi Kazuhiko et al, "Performance of a Coiled Capillary on One–cm Diameter in Capillary Electrophoresis" Analytical Sciences, vol. 12 (Oct. 1996) 811–814.

Kevin D. Altria, "Micro–Preparative Applications of Capillary Electrophoresis" Isolation & Purification, vol. 2 (1996) 113–125.

Y. Chen & An Zhu, "Flat Capillary Zone Electrophoresis" Science in China (Series B) vol. 35, No. 6 (Jun. 1992) 649–658.

Kevin D. Altria, "Optimization and Improvement of Sensitivity in Capillary Electrophoresis for Quantitation of Selected Pharmaceutials" LC–GC, vol. 11 No. 6 (Jun. 1993) 438–442.

Huey G. Lee, "Optimization of the Loading Limit for Capillary Zone Electrophoresis of Synthetic Opioid and Tachykinin Peptides: a Study of the Interactions Among the Amount of Peptide, Resolution, Saturation, Injection Volume and Capillary Diameter" Journal of Chromatography B, 662 *(1994) 35–45.

Keely et al. Dec. (1994) "Modeling Flow Profiles and Dispersion in Capillary Electrophoresis with Nonuniform Potential", *Analytical Chemistry*, 66(23), pp. 4236–4242.

(List continued on next page.)

*Primary Examiner*—Kathryn L. Gorgos
*Assistant Examiner*—John S. Starsiak, Jr.

[57] ABSTRACT

A wide-bore capillary electrophoresis apparatus for the analysis of analyte ions is provided. The apparatus has a wide-bore capillary that has a restriction zone at one or more ends. The capillary has an inlet end and an outlet end and an opening at each of said ends. The restriction zone is capable of providing fluid communication between the wide bore and the opening at said end. The restriction zone includes a narrow bore extending to the opening and a transition zone providing gradual change of bore diameter from the wide bore to the narrow bore. The apparatus further has a buffer source to supply buffer to the inlet end of the capillary and a power supply for supplying power to drive buffer and analyte ions through the capillary. During CE, electrodes provide electrical communication between the power supply and the inlet end and the outlet end and apply a voltage differential between said ends.

18 Claims, 12 Drawing Sheets

OTHER PUBLICATIONS

Datta et al. Jun. (1990) "Electrokinetic Dispersion in Capillary Electrophoresis", *AIChE Journal*, 36(6), pp. 916–926.

Brown et al. No month available (1975) "Electrophoretic Thermal Theory II. Steady–State Radial Temperature Gradients in Circular Section Columns", *J. of Chromatography* 109, pp. 218–224.

R. Aris. (1995) No month available "On the Dispersion of a Solute in a Fluid Flowing Through a Tube", *Dept. of Chem, Eng., Univ. of Minnesota*, pp. 67–77.

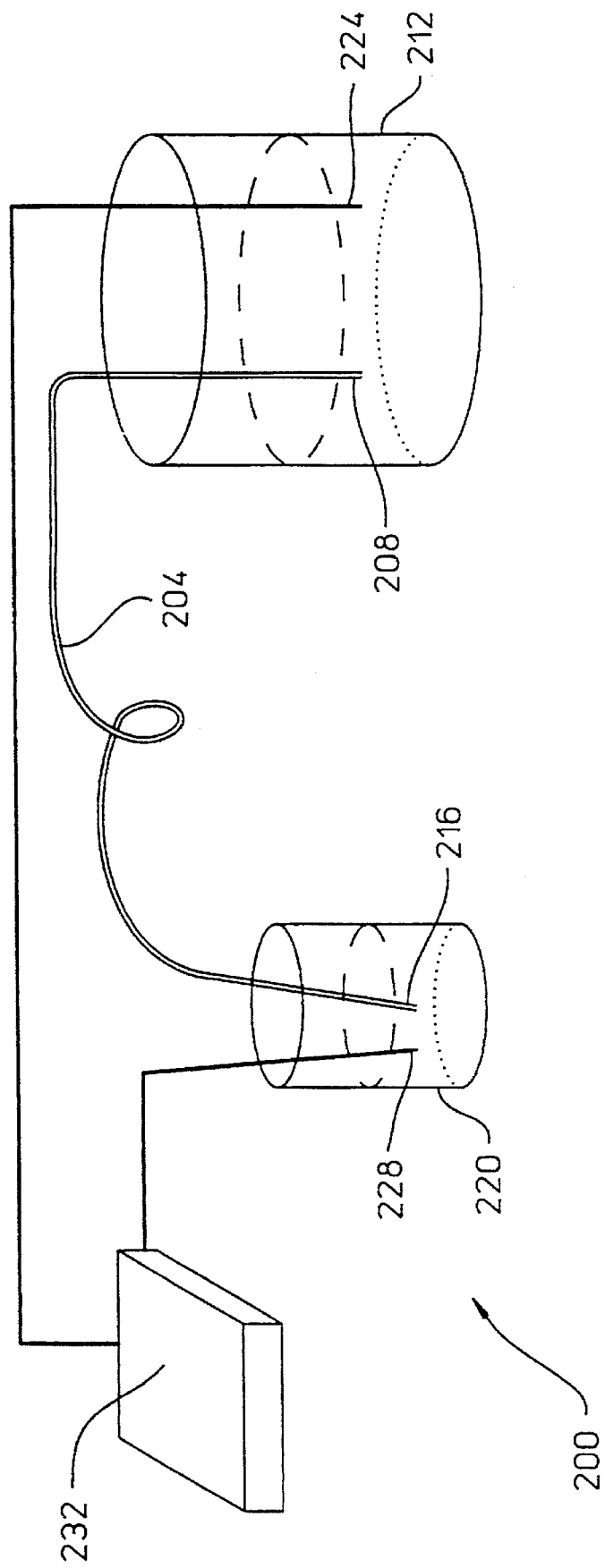

PREPARATIVE CAPILLARY ELECTROPHORESIS WITH WIDE-BORE CAPILLARY

BACKGROUND

This application is filed under 35 U.S.C. § 119(e) for an invention disclosed in and claims priority of the provisional application (application Ser. No. 60/010,396) filed on Jan. 22, 1996.

The present invention is related to capillary electrophoresis, more particularly to capillary electrophoresis using a wide-bore capillary.

Capillary electrophoresis (CE) has found wide acceptance in the analytical sciences, with application in diverse fields, including pharmaceutical analysis and bioscience research. Frequently CE has been called upon to provide semi-preparative quantities for further analysis, such as for microsequencing or mass spectrometry (MS) analysis. Bundled capillaries, multiple injections combined with fraction collection, and larger capillaries have all been used with some success to provide nanomolar quantities of analytes, but these approaches have for the most part resulted in reduced performance of the CE system. Clearly the need exists for capillary separation methods to more closely match the input loading requirements of the analytical techniques with which they are mated.

An approach to increased loadability in CE is increasing the injected volume. Two methods could be used: (A) in a standard (e.g. 75 μm i.d.) column (i.e., capillary), increasing the mount injected into the column, thereby increasing the injection plug length; and (B) increasing the inside diameter (i.d.) of the column (e.g., to 150-200 μm) to keep the injection plug length constant for an increased sample loading. However, studies have indicated rapid decreases in separation efficiency when either of these two approaches are attempted.

BRIEF DESCRIPTION OF THE DRAWINGS

The following figures are included to better illustrate the embodiments of the apparatus of the present invention. In these figures, like numerals represent like features in the several views.

FIG. 11 shows an isometric view of an embodiment of the CE apparatus of the present invention.

DISCLOSURE OF THE INVENTION

We have found that by restricting the end portion(s) of the bore (i.e., lumen) of a wide-bore capillary, siphoning can be substantially avoided, thereby enabling the application of wide-bore capillaries, i.e., capillaries with a bore larger than the standard bore of about 75 μm i.d., for CE analysis.

Several mechanisms by which band broadening may quickly increase in wide-bore capillaries were investigated: (1) siphoning between electrode reservoirs; (2) temperature effects due to Joule heat, including both radial temperature profile and average buffer temperature; and (3) pH changes within the buffer reservoirs due to the increased electrical current in a wide bore. This disclosure considers these mechanisms individually in wide-bore capillaries, and provides practical solutions which can result in successful analyte separations on such capillaries. Our results demonstrate (as shown in FIG. 1) that with appropriate attention to these factors good system performance can be obtained, and that the increased loadability of wide-bore capillaries permits much more practical injection volumes when fraction collection is required.

Figure 1:
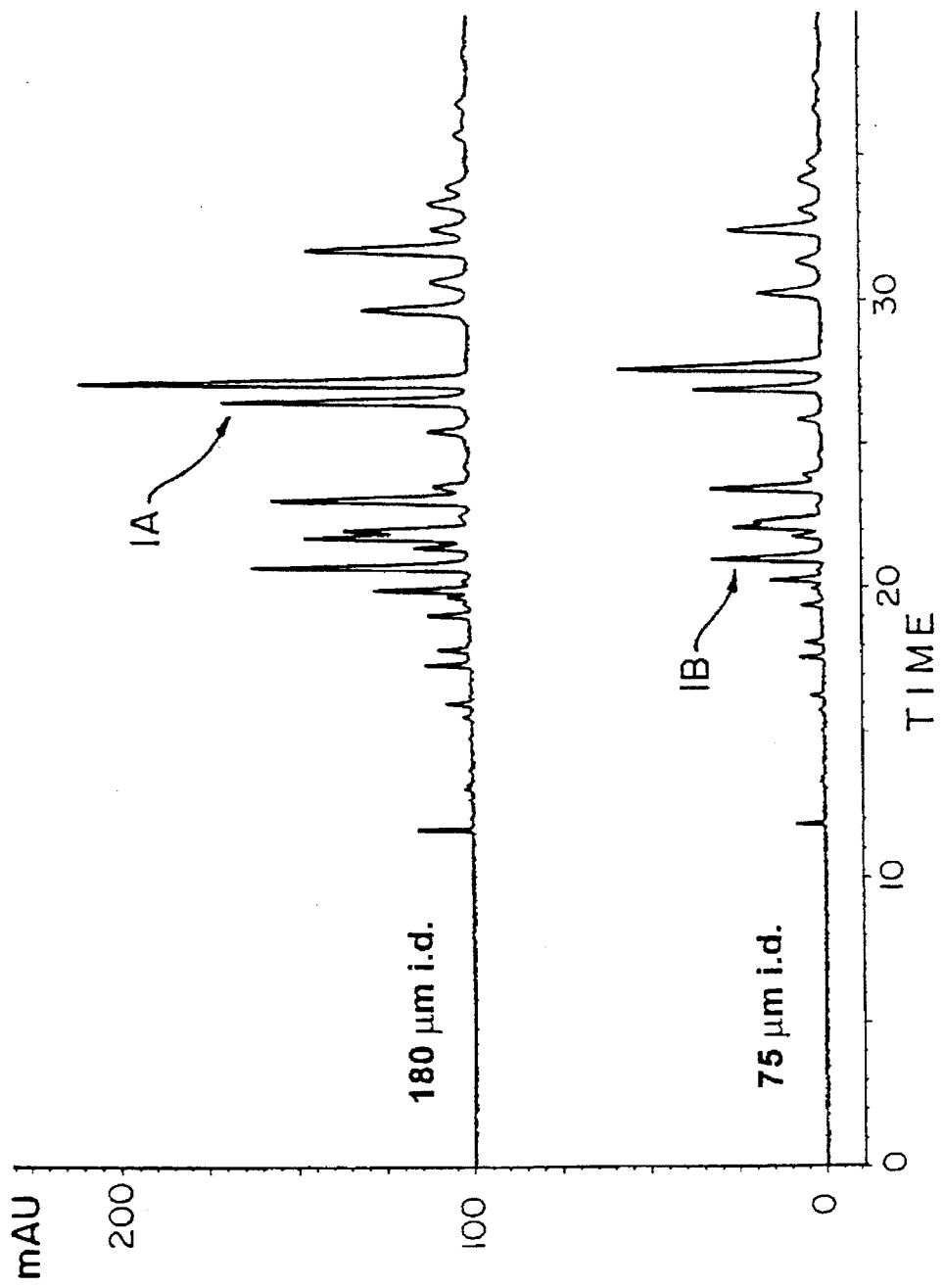
FIG. 1 shows the result of CE separation of rhGH tryptic digest with a standard 75 μm i.d. capillary compared to a 180 μm i.d. capillary of the present invention.

In FIG. 1, the bottom curve 1B shows the CE result using a standard 75 μm i.d. capillary and the top curve 1A shows the CE result using a wide-bore (180 μm i.d.) capillary in accordance of the present invention. The effective length of each capillary is 41.5 cm and the total length of each capillary is 50 cm. In the wide-bore capillary, each end is restricted with a 50 μm i.d. restrictor. The two curves shows comparable separation efficiency. This indicates that the presence of restrictors results in good CE performance even when a wide-bore capillary is used. The run parameters are described in the following:

Buffer: 100 mM phosphate, pH 2.0.
Injection: pressure.
Detection: UV 200 nm.
High voltage: constant current mode
  52 μA and 7.0 kV for 75 μm i.d. capillary,
  300 μA and 7.4 kV for 180 μm i.d. capillary.
CE instrument: HP1601A HP$^{3D}$CE.

Separation Efficiency for Large Sample Volumes

Figure 2A:
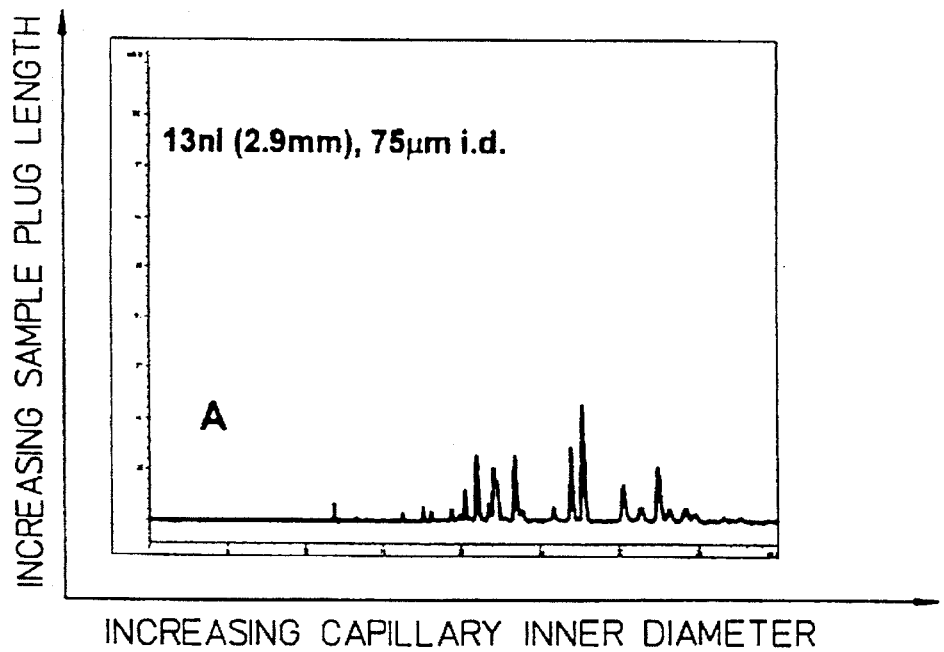
FIG. 2A shows the result of CE separation of rhGH tryptic digest with a standard 75 μm i.d. capillary with a 13 nL injection volume.
Figure 2B:
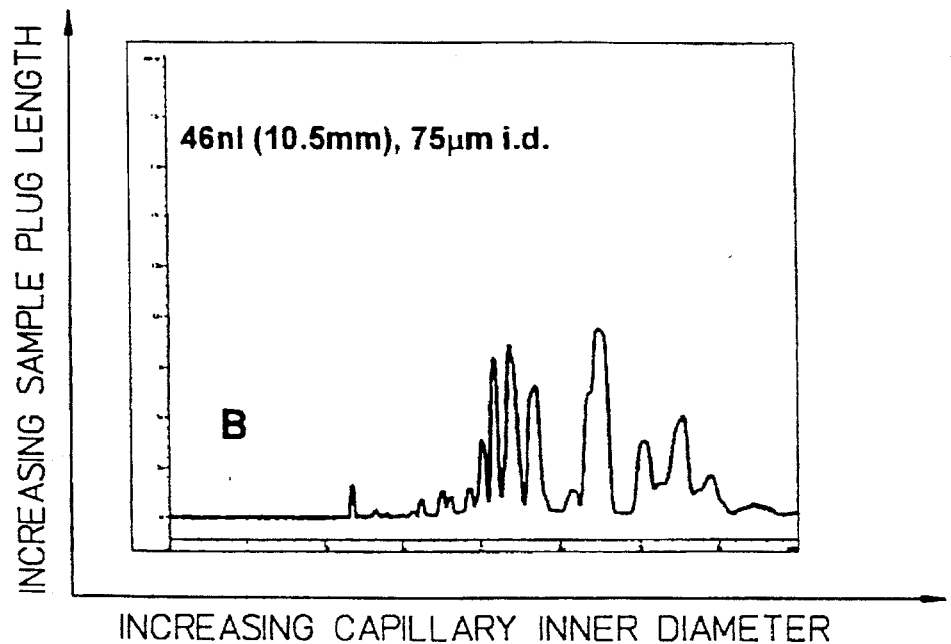
FIG. 2B shows the result of CE separation of rhGH tryptic digest with a standard 75 μm i.d. capillary with a 46 nL injection volume.
Figure 2C:
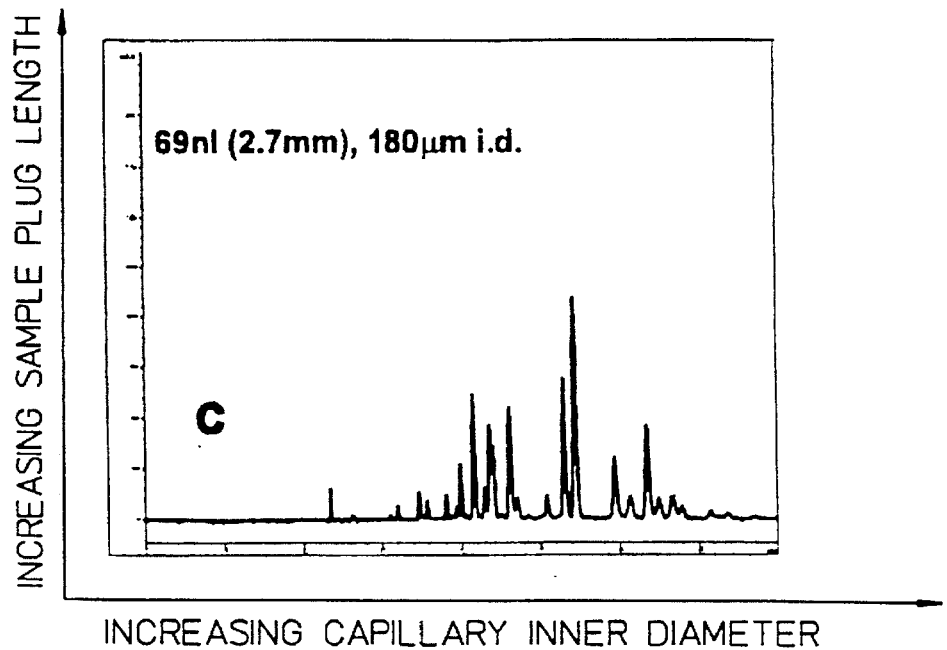
FIG. 2C shows the result of CE separation of rhGH tryptic digest with a 69 nL injection volume to a 180 μm i.d. capillary of the present invention.
Figure 2D:
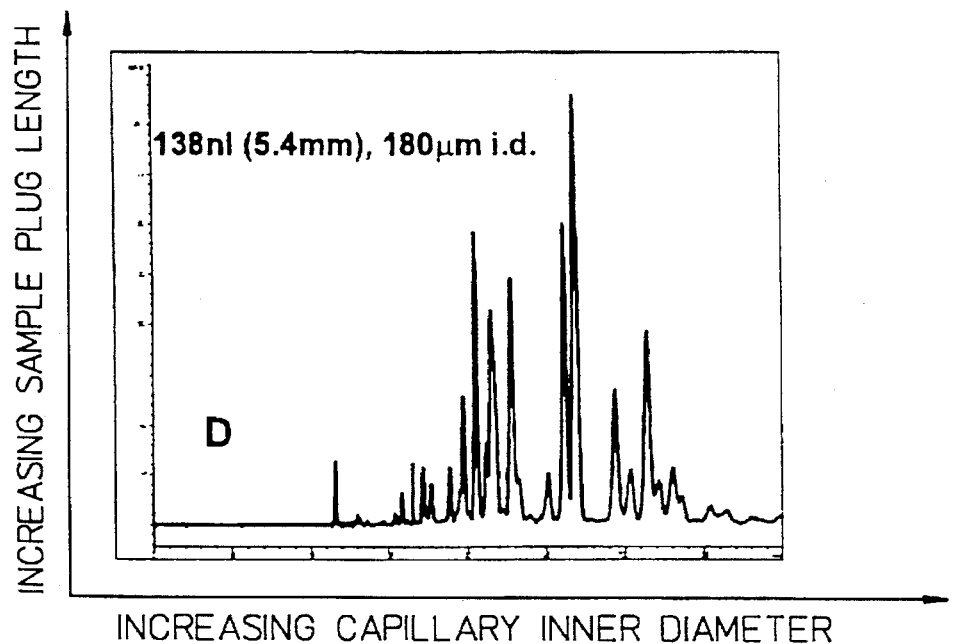
FIG. 2D shows the result of CE separation of rhGH tryptic digest with a 138 nL injection volume to a 180 μm i.d. capillary of the present invention.

Although it is possible to inject greater volumes into standard diameter (e.g., 75 μm i.d.) CE capillaries for increased sample loading, this can only be used to a very limited degree. The increased injection volume results in an increased injection plug variance, which would soon become the dominating plate height (i.e., the theoretical plate height, hereinafter referred to as "plate height") contributor. With increased injection volume, separation efficiency will suffer because the limiting efficiency of capillary systems is determined by the ratio of the injected volume to the analytical volume of the system. FIGS. 2A–2D show the effect plug length and capillary i.d. have on the CE separation efficiency. FIG. 2 (A, B) illustrates the problem of increased i.d.: in a 75 μm i.d. capillary a 46 nL injection volume (10 mm injection plug length) will effectively destroy the separation (FIG. 2B) whereas a 13 nL injection volume gives acceptable result (FIG. 2A). However, with the restricted capillaries of the present invention, increased inside diameter (i.d.) of the capillary can produce good CE separation, since the injected volume increases as the square of the diameter and the increased injection volume can be accommodated with no increase in injection plug length. For example, an increase in capillary diameter, from 75 to 180 μm, would increase the injected volume by a factor of about 6 with no change in injection plug length and therefore with no change in separation efficiency (comparing FIG. 2A with FIG. 2C, which involves a 180 μm i.d. capillary with a 69 nL injection volume). With the restricted 180 μm i.d. capillary of the present invention, injection volumes of up to 138 nL (5.4 mm plug length) have been used, with only minimal degradation of separation efficiency (FIG. 2D).

1. Prevention of Siphoning in Wide-Bore Capillaries

When using wide-bore capillaries, the wider bore, i.e., larger bore, reduces the flow resistance and, as a result, the flow through the capillary due to siphoning can be significant. Because the flow is pressure-driven, siphoning can cause large changes in velocity and can increase band broadening. This effect was examined theoretically and experimentally. It was found that by modifying the capillary with flow restrictors, siphoning effects were greatly reduced.

In a standard capillary, i.e., nonrestricted capillary normally used in the art, the change in velocity will vary linearly with the pressure head, and with the square of the diameter (see, e.g., Keely, C. A; van de Goor, T. A. and McManigill, D., Anal. Chem., 66(1994), 4236–4242; Aris, R., Proc. R. Soc. London, A235(1956), 66–77; Datta, R. and Kotamarthi, V. R., AICHE J., 36(1990), 916–926, which are incorporated by reference herein).

$$\Delta v(r,p) = \frac{p r_i^2}{8 \eta L}(1-2r^2) \qquad \text{Eq. 1}$$

The plate height function is more complicated, but in wider-bore capillaries, plate height will increase linearly with pressure, and with the fourth power of the diameter.

$$H = \frac{2}{u} K_d \qquad \text{Eq. 2}$$

where $$K_d = D - \frac{2r_i^2}{D} \int_0^1 \left( \int_0^r \frac{1}{r'} \left( \int_0^{r'} \Delta v(r'') r'' dr'' \right) dr' \right) \Delta v(r) r \, dr \qquad \text{Eq. 2a}$$

In the equations in this disclosure, the variables are:

D = diffusion coefficient
H = plate height $J_0, J_1$ = Bessel function of first kind, order 0 and 1
$K_d$ = total dispersion
$k_1, k_2$ = thermal conductivity of buffer and fused silica
L = total length of capillary
p = pressure
r = normalized radius variable
$r', r''$ = integration variables representing r
$r_i, r_0$ = capillary radius, inside and outside
$T_0$ = temperature outside capillary
$\Delta T$ = temperature difference, center to wall
u = average bulk velocity
$\Delta v$ = change in velocity function
$w_0$ = power dissipated
α = temperature coefficient of resistivity
η = viscosity of buffer
μ = −α

Thus, siphoning can severely impact the separation efficiency in wide-bore capillaries.

Figure 3:
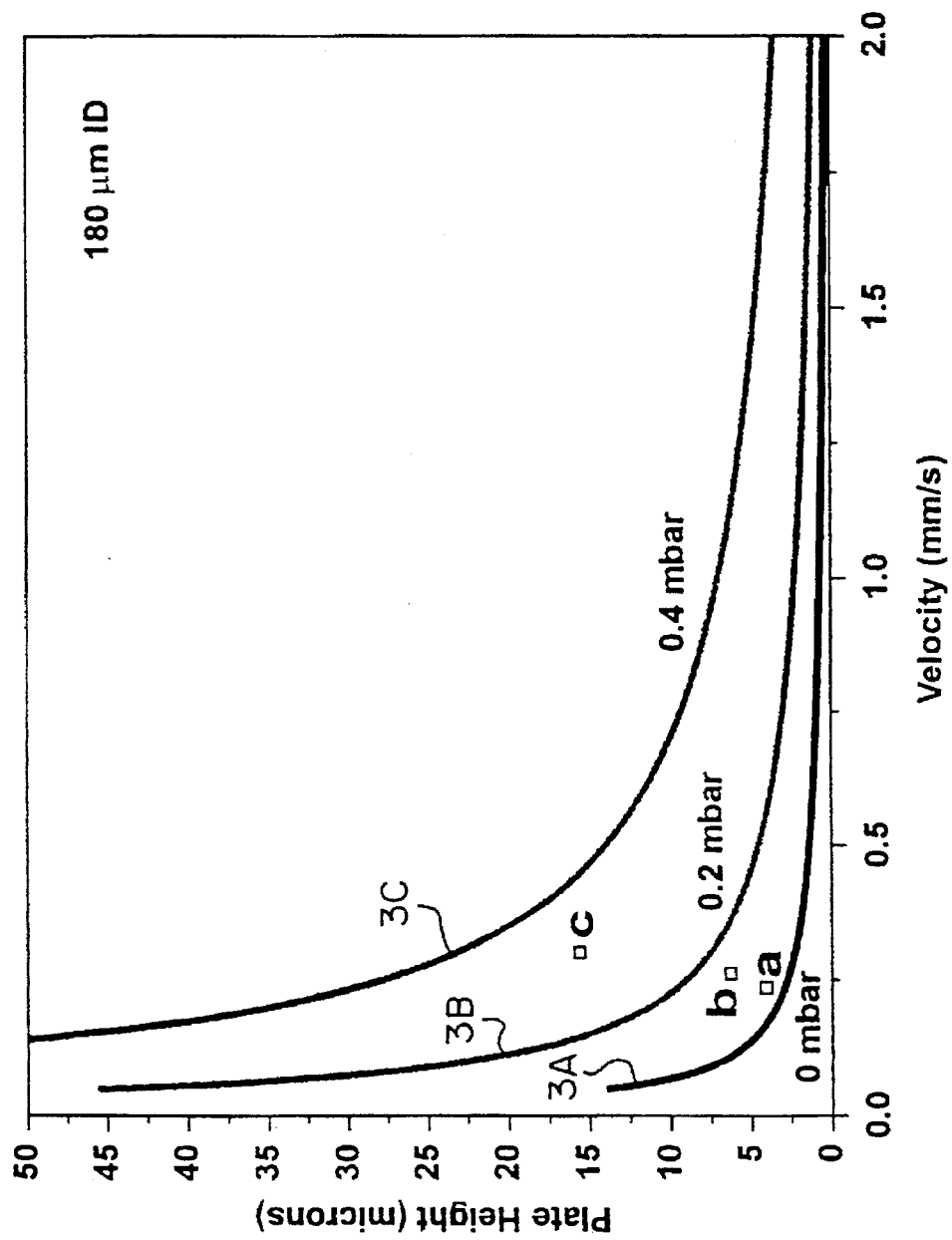
FIG. 3 shows the graphical representation of plate height as a function of velocity with different amounts of siphoning pressure, determined theoretically for a 180 μm i.d. straight (unrestricted) capillary and showing data points a, b, c for a restricted 180 μm i.d. capillary.

FIG. 3 gives the plate height as a function of velocity for a 50 cm straight 180 μm i.d. capillary, assuming that only diffusion and the pressure flow profile contribute to the plate height. The three curves represent different amounts of siphoning via pressure heads (inlet above outlet): 0 mm (shown by the bottom curve 3A), 2 mm (0.2 mbar, middle curve 3B), and 4 mm (0.4 mbar, shown by the top curve 3C). As expected, even a small pressure head causes enough siphoning to greatly increase the plate height in this column. By comparison, the pressure head would have to be 30 mm (3 mbar) in a 75 μm i.d. capillary to generate the plate heights given in the 0.2 mbar curve (middle curve, 3B). Data points a, b, and c are for a capillary according to the present invention corresponding to the three siphoning pressures and will be described infra.

To make a capillary that has little siphoning (i.e. reduced siphoning compared to a capillary with the same capillary i.d.), according to the present invention, the ends of the wide-bore capillaries are heated (e.g. by a flame) to soften the capillary such that the ends gradually collapse to narrow the bore to a desired geometry with a slender narrow bore (or restriction) proximate the very end of the capillary. In the restriction, the bore gradually increases in diameter (such as through a transition portion) to the size of the full wide-bore of the capillary. This heating and bore-narrowing procedure is referred to as "flame restricting" herein. Typically, an end of the capillary is heated in a relatively uniform fashion such that the restriction can be formed with a generally straight centerline (or axis) with circular cross section. For example, during flame-restricting, the end portion of the capillary can be heated and rotated in a flame while its geometry is being monitored in a microscope. It is contemplated that the end portion can also be held and drawn to facilitate the formation of the narrow bore. Automated equipment can be used to make such restrictions on the ends of capillaries.

Figure 4:
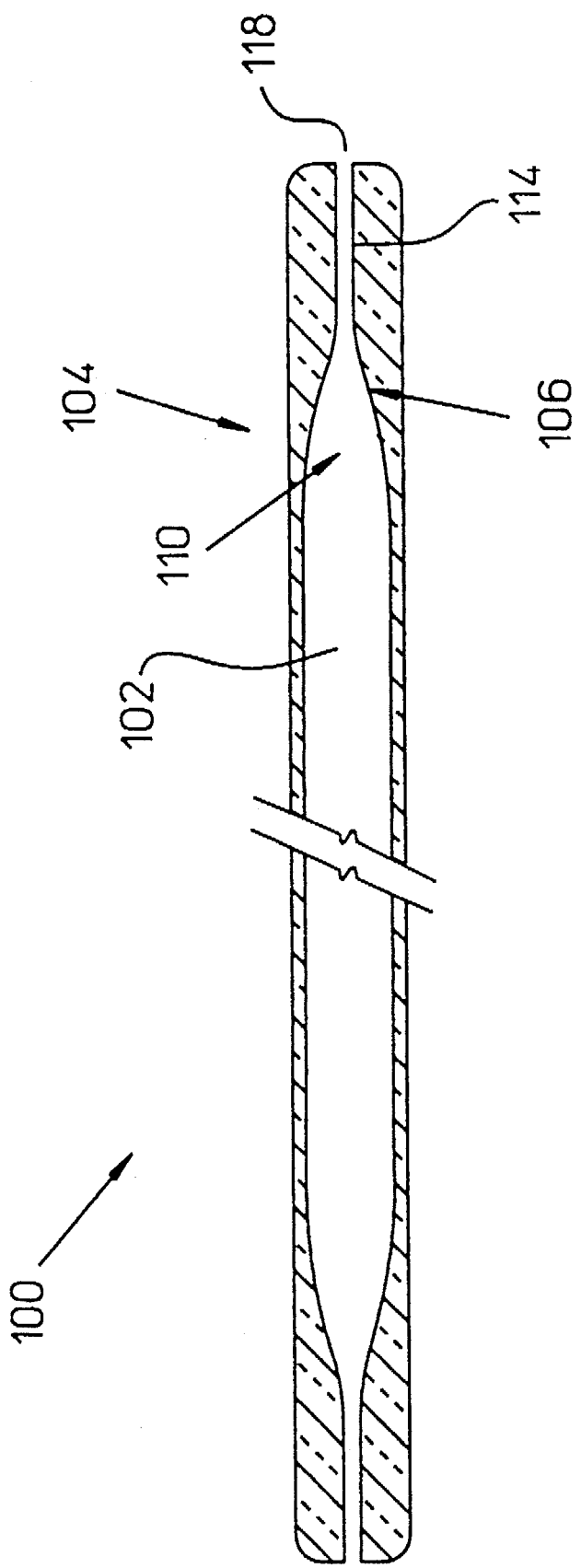
FIG. 4 shows a sectional view (along the axis) of an embodiment of the restricted capillary of the present invention.

An embodiment of a capillary in accordance of the present invention is shown in FIG. 4. The capillary has a wide-bore 102. The capillary 100 also has at least one end 104 that has a restriction 106 to reduce siphoning during CE. The restriction 106 preferably has a transition zone 110 that gradually narrows to a slender narrow-bore 114 that extends for a length to an opening 118 that provides fluid communication with the outside. Preferably, the capillary has a restriction on each end of the capillary. The capillary has a wide bore (i.e., with an i.d. equal to or larger than about 75 μm), which preferably has an i.d. of about 100 to 500 μm, more preferably about 100 to 250 μm, even more preferably about 180 to 200 μm.

The size of the restriction is selected to reduce siphoning to an acceptable level. As an example, for a capillary with about 50 cm total length, about 40 cm effective length, and a CE voltage of about 7 kV, the short restriction formed can be about 10 to 1000 μm long and about 20 to 75 μm i.d., preferably about 250–750 μm long and 20 to 50 μm i.d., more preferably about 0.5 mm long with an i.d. of 50 μm. The selection of the length and i.d. of the restriction depends on factors such as the length and i.d. of the capillary, as well as the voltage applied for CE. A person skilled in the art will be able to select these parameters based on the present disclosure. It is understood that although the restriction is preferably integrally connected to the wide-bore part of the capillary (as in flame-restriction the wide-bore capillary), the restriction can be a separate piece connected to the wide-bore portion by a fitting, by adhesion, as a plug, and the like. The restricted capillary of the present invention can be made with standard materials that are used for making CE capillaries, for example, nonmetallic inorganic material (e.g., fused silica), polymeric material such as polytetrafluoroethylene (PTFE), polyether ether ketone (PEEK), and the like.

Capillaries of the above sizes and shapes can reduce the effects of siphoning to an acceptable amount. For example, the 180 μm i.d. capillary with end restrictions of about 0.5 mm long with an i.d. of 50 μm is comparable to a 135 μm i.d. capillary in separation efficiency. A further technique to reduce siphoning is to balance the levels of the buffer reservoirs in which the electrodes are located. The buffer replenishment feature of the HP$^{3D}$CE apparatus permits such buffer leveling of the reservoirs, which, together with the modified capillaries, results in improved reproducibility of the migration time and peak area, as well as better control of pressure injections and fraction collection.

Figure 5:
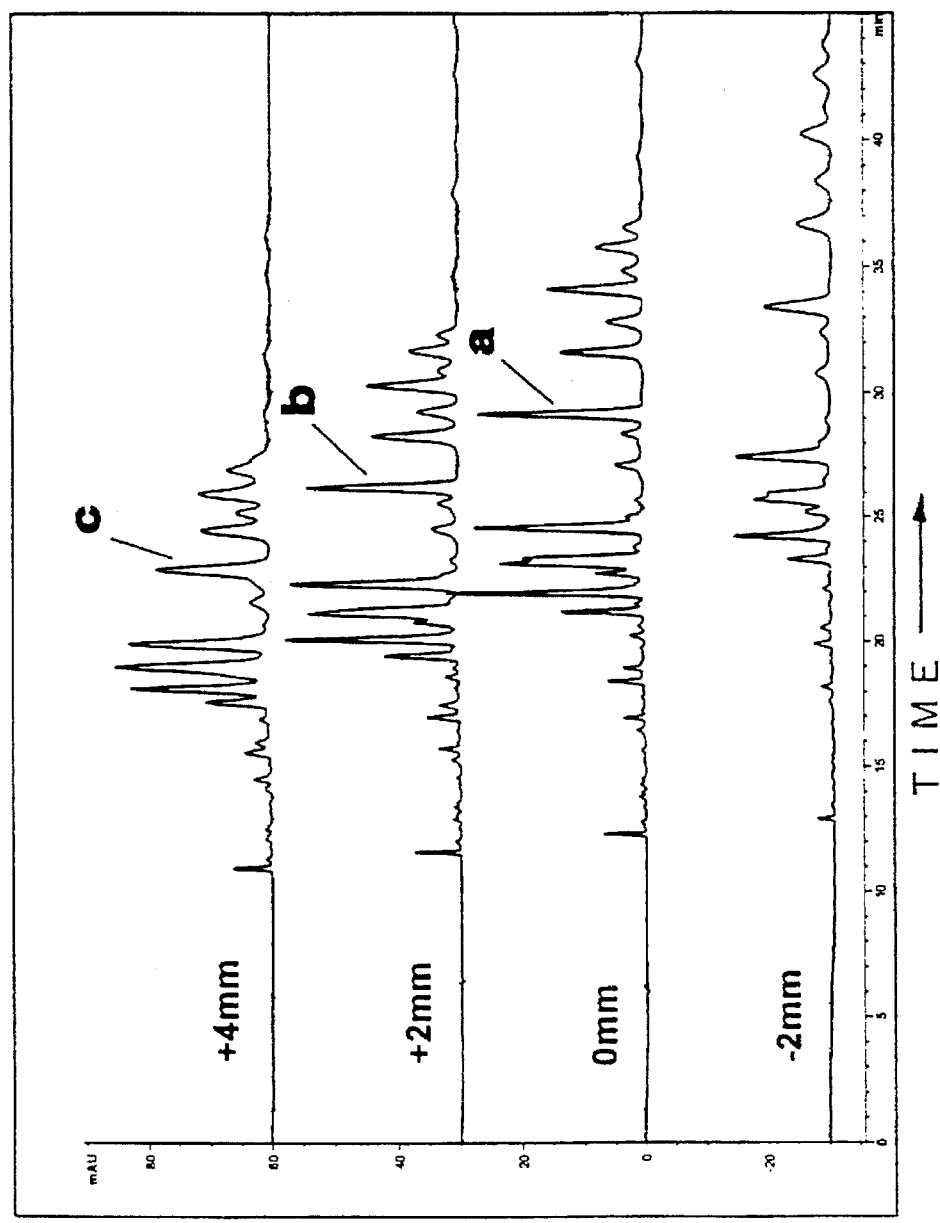
FIG. 5 shows the result of CE separation of rhGH tryptic digest with a 180 μm i.d. capillary of the present invention at different pressure heads.

FIG. 5 demonstrates the separation of analytes in a 180 μm restricted capillary (having 0.5 mm long restriction with an i.d. of 50 μm) with imposed pressure head of 0 mm (associated with peak a), 2 mm (associated with peak b), and 4 mm (associated with peak c). The velocity and plate heights calculated from the indicated peaks are plotted in FIG. 3. From FIG. 3, it can be seen that the theoretical data points a, b, and c, which correspond to the peaks a, b, and c for a restricted capillary in FIG. 5, are indeed much lower than those in the theoretical curves, i.e., curves 3A, 3B, and 3C, for the non-restricted capillary. In fact, CE analysis with parameters used in the runs of FIG. 5 could not be done using a straight bore capillary of 180 μm, due to the siphoning effects, as well as large changes in migration time.

2. Temperature Effects

A concern for CE analysis using a wide-bore capillary is the detrimental effect (band broadening) on separation caused by nonuniform temperature in the capillary. For a given applied CE voltage, the electrical current through the capillary increases with the square of the diameter, thus wide-bore capillaries of average length (as in conventional small-bore capillaries) in CE require a larger electrical current, which leads to a large power dissipation in the capillary. This power is dissipated as Joule heating, and leads to a radial temperature gradient and an increased average temperature. We have found that using a restricted wide-bore capillary of the present invention to analyze peptide sized molecules the actual increase in plate height is negligible.

(a) Radial Temperature Profile

The radial temperature gradient is a function of the power dissipated, capillary dimensions, thermal characteristics of the buffer and capillary, and the external temperature. This radial temperature gradient can be calculated (Brown, J. F. and Hinckley, J. O. N., J. Chromatogr., 109(1975), 218–224, which is incorporated by reference herein):

$$T(r) = \frac{J_0(\beta r)}{J_0(\beta r_i)} \left( T_0 + \frac{1}{\mu} + \frac{w_t}{2\pi k_2} \ln\left(\frac{r_0}{r_i}\right) \right) - \frac{1}{\mu} \quad \text{Eq. 3}$$

with $$w_t = \left( \frac{2\pi \mu w_0 r_i k_2 J_1(\beta r_i)}{\beta k_2 J_0(\beta r_i) - \mu w_0 r_i \ln\left(\frac{r_0}{r_i}\right) J_1(\beta r_i)} \right) \left( T_0 + \frac{1}{\mu} \right) \quad \text{Eq. 3a}$$

$$\beta = \frac{\sqrt{\mu w_0}}{k_1} \; ; \mu = -\alpha \quad \text{Eq. 3b}$$

Figure 6:
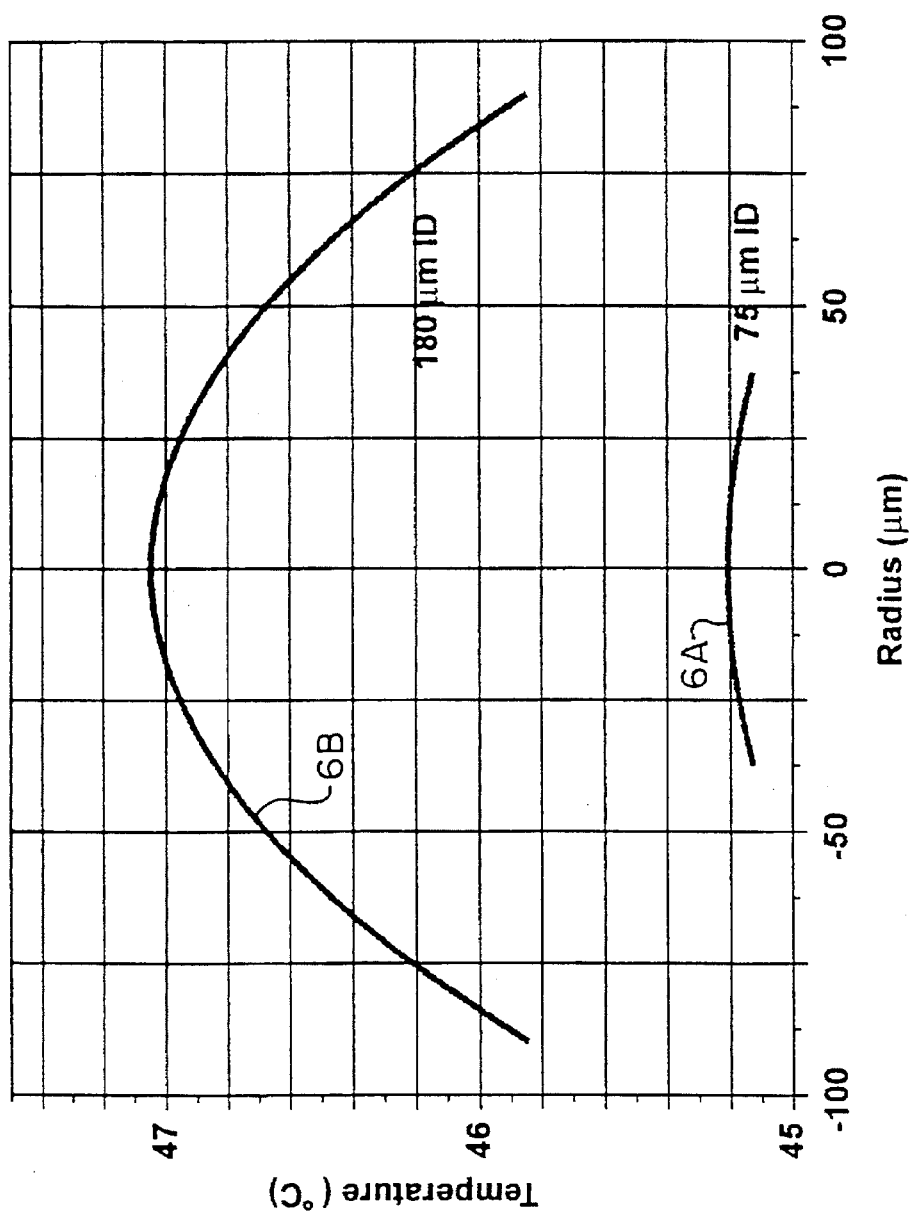
FIG. 6 shows a graphical representation of the temperature profile inside a 75 μm i.d. capillary compared to that inside a 180 μm i.d. capillary.

FIG. 6 shows the thermal profiles calculated for 180 μm i.d. (curve 6A) and 75 μm i.d. (curve 6B) capillaries with the external temperature at 45° C. Although the 180 μm gradient is much larger than that of the 75 μm, there is still only 1.2° C. difference between the temperature of the outside wall and that at the center. The resultant plate height can be calculated by assuming the temperature profile causes a viscosity profile, which in turn causes a parabolic velocity profile (Eq. 2, 4).

$$\Delta v(r, \Delta T) = \frac{\mu \Delta T \hat{u}}{2} (1 - 2r^2) \quad \text{Eq. 4}$$

Figure 7:
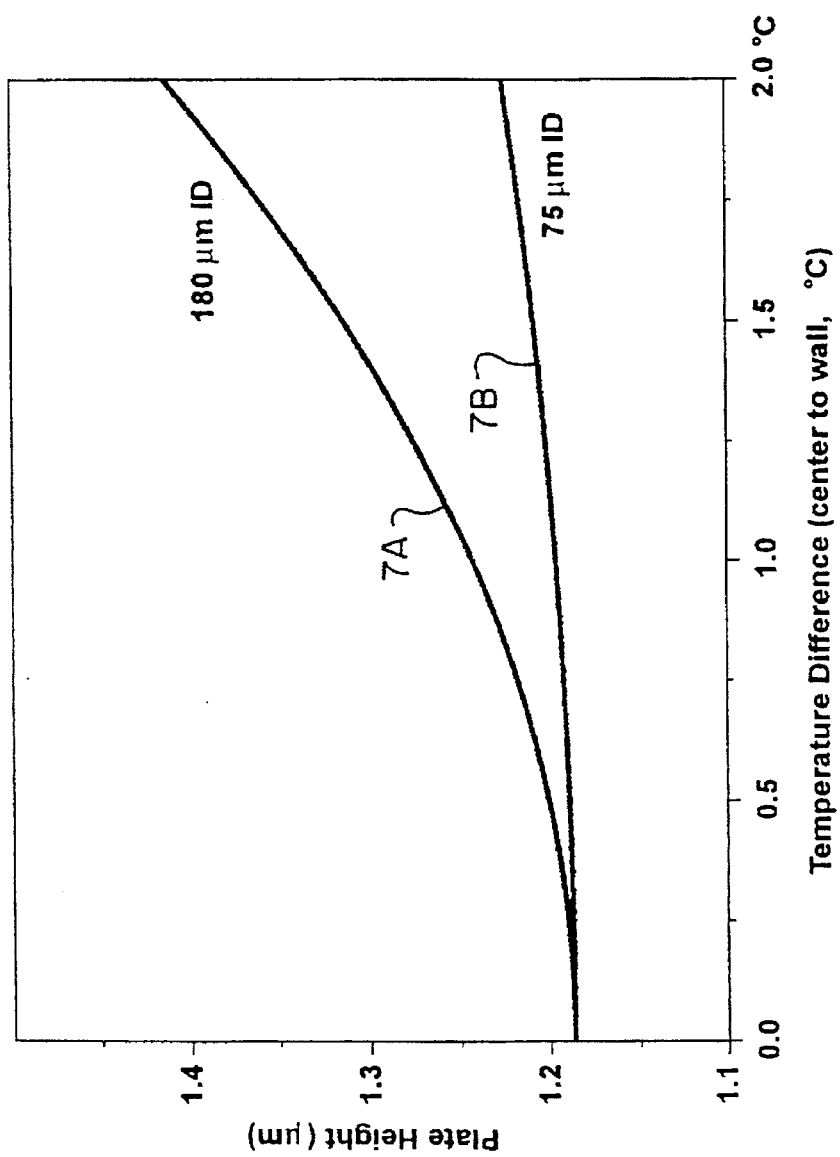
FIG. 7 shows a graphical representation of the plate height as a function of the radial (axis to wall) temperature difference for a 75 μm i.d. capillary and for a 180 μm i.d. capillary.

FIG. 7 shows the theoretical plate height as a function of the difference in temperature between the wall and the center, assuming the velocity changes 2% per °C. and assuming a diffusion coefficient representative of peptides. As shown in FIG. 7, although the effect on plate height is greater for a 180 μm capillary (curve 7A) than for a 75 μm capillary (curve 7B), it is still less than 0.1 μm for the predicted temperature difference of 1.2° C. This effect (i.e., contribution to increase plate height by temperature difference) will be negligible, especially when the contribution to plate height due to the finite injection volume is taken into account.

In a system which has siphoning in addition to a temperature profile, the increase in plate height will be greater than the sum of the two plate height effects because the profiles will interact with each other. This is why reducing siphoning is so important in reducing band broadening.

(b) Average Buffer Temperature

Because CE is effected by an electrical potential difference applied to the two ends of the capillary, heat is dissipated in the capillary. For example, three watts of energy dissipated in a 375 μm i.d. 180 μm i.d. capillary will raise the average temperature inside the capillary by about 20° C. over the control temperature when forced air cooling is used. Furthermore, mounting and sealing points inaccessible to cooling may form hot spots where the buffer may boil. Fixture designs that allow proper cooling can minimize hot spots. We have found that for a capillary of the present invention, the average temperature does not significantly affect the CE separation.

Figure 8:
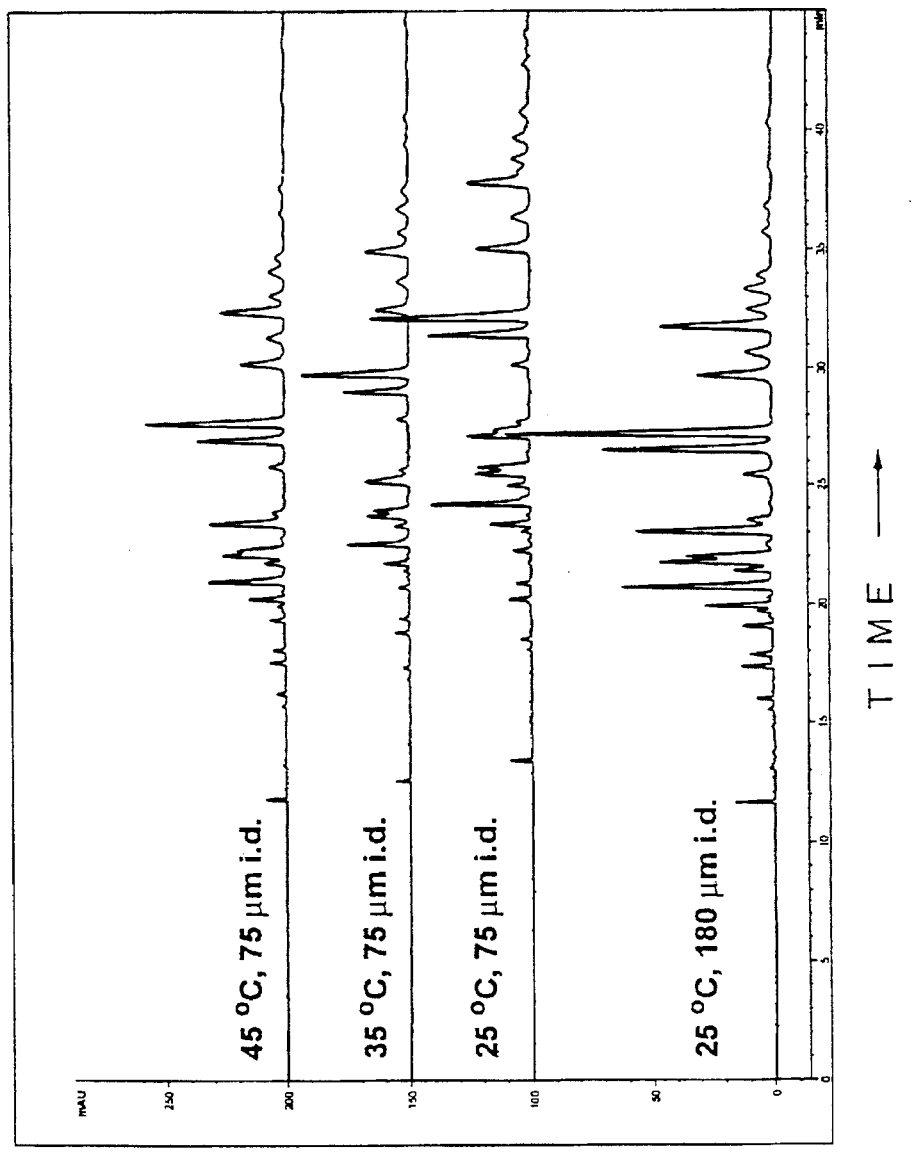
FIG. 8 shows the result of CE separation of rhGH tryptic digest with a 180 μm i.d. capillary of the present invention at 25° C. and with a standard 75 μm i.d. capillary at 25° C., 35° C., and 45° C.

FIG. 8 shows the results of analyte separations done using a restricted 180 μm i.d. capillary with the control temperature held at 25° C. and also in a 75μm capillary with control temperatures of 25° C., 35° C. and 45° C. Comparison of the velocities and efficiencies indicates that the inside of the 180 μm, 25° C. capillary is approximately the same temperature as inside the 75 μm, 45° C. capillary. There is no significant difference in band broadening between the four runs, indicating that the average temperature increase is not a problem for this separation. This figure also supports the theoretical prediction that the temperature gradient effect on plate height is negligible.

3. Buffer Depletion due to Coulombic Titration

Because up to 300 µA current is often applied for wide-bore capillary electrophoresis, buffer depletion due to coulombic titration occurs much faster in such wide-bore capillaries than in standard capillaries. For example, Table 1 shows the pH change of 100 mM pH 2.5 phosphate buffer during electrophoresis for given volumes of buffer when 300 µA current is applied. To reduce buffer depletion, 4–5 mL triple vials (i.e., vials three-times the size of normal vials) were used. Using these vials, a two hour run at 300 µA resulted in a buffer pH change of less than 0.1 pH units.

TABLE 1

|        | 30.0 min | 60.0 min | 90.0 min | 120.0 min |
|--------|----------|----------|----------|-----------|
| 0.5 ml | 0.198    | 0.420    | 0.709    | 1.268     |
| 1.0 ml | 0.098    | 0.198    | 0.304    | 0.420     |
| 2.0 ml | 0.049    | 0.098    | 0.148    | 0.198     |
| 4.0 ml | 0.024    | 0.049    | 0.073    | 0.098     |

Applications

Figure 9:
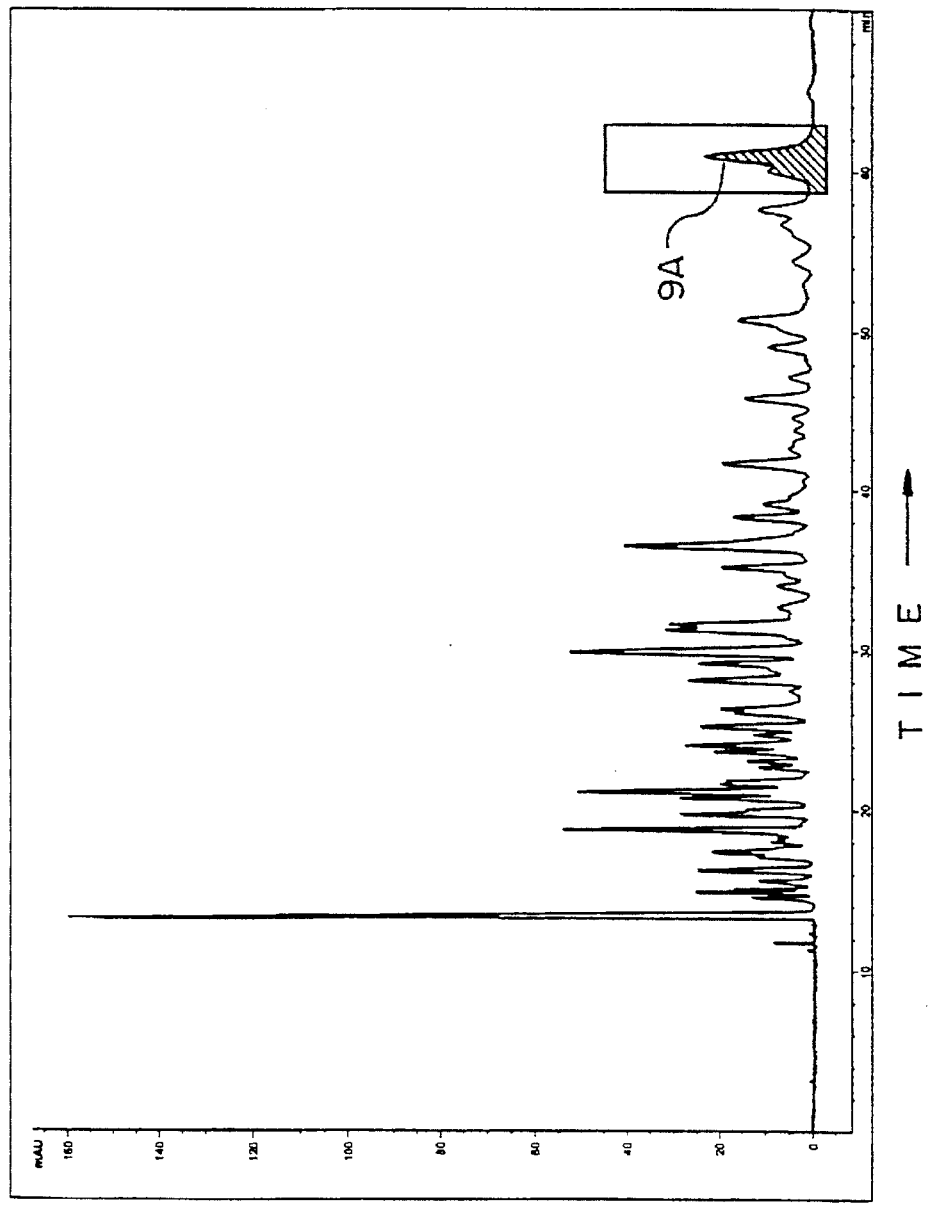
FIG. 9 shows the result of CE separation of rtPA tryptic digest and fraction collection using a 180 μm i.d. capillary of the present invention.
Figure 10:
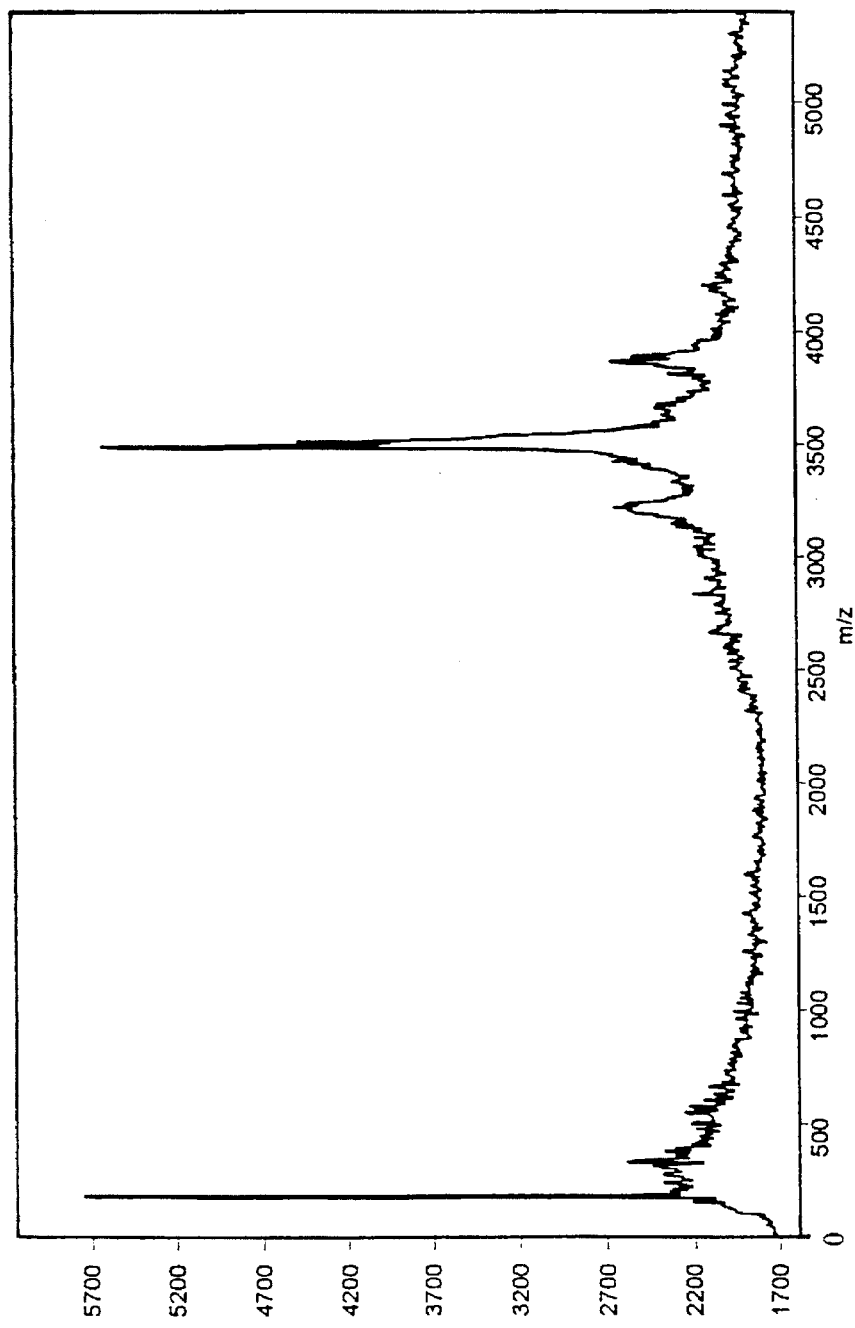
FIG. 10 shows the mass spectrum of MALDI-TOF mass spectrometry of the collected fraction 9A of FIG. 9.

The capillaries and CE apparatus of the present invention can be used for analyzing analytes as in using a conventional CE apparatus. The large sample volume injections allow complex samples to be analyzed with adequate material in the individual peaks to permit subsequent analyses, without sacrificing resolution. As an example, tryptic digest of rtPA was analyzed with a modified 180 µm i.d. capillary (FIG. 9). The fraction marked as 9A (shaded) was collected from the capillary using 25 mbar pressure for 12 seconds immediately after the peak was detected. Matrix-assisted laser desorption ionization-time of right mass spectrometry (MALDI-TOF MS) can be used to analyze the fractions collected. Such an analysis identified this fraction as a glycopeptide fragment (T45) of the rtPA digest (FIG. 10). The CE columns (i.e., capillaries of the present invention), due to their increased loadability, are more suitable than standard capillaries to permit a complimentary match between CE and emerging micro LC systems, interfacing techniques for hyphenated instruments, and semi-preparative sample production. This in turn would facilitate the construction of a unified apparatus for micro separations work of high sensitivity and separation efficiency.

To use a restricted capillary of the present invention, standard equipment for CE can be adapted for use with a wide-bore application. Such CE equipment and methods are known in the art. An example of CE equipment that can be adapted for a wide-bore capillary of the present invention is HP1601A HP$^{3D}$CE (Hewlett Packard Co., Palo Alto, Calif). CE equipment in accordance of the present invention is illustrated in FIG. 11. In the CE apparatus 200 shown in FIG. 11, a wide-bore capillary 204 has one end (e.g., inlet end) 208 immersed in a buffer in a first container (e.g., buffer supply) 212 and another end (e.g., outlet end) 216 immersed in a buffer in a second container (e.g., collection bottle) 220. A first electrode 224 is immersed in the buffer in the first container 212 and a second electrode 228 is immersed in the buffer in the second container 220 to provide a voltage differential for driving CE. The first electrode 224 and the second electrode 228 are electrically connected to a voltage supply 232 that provides the power to drive CE.

What is claimed is:

1. A wide-born capillary electrophoresis (CE) apparatus for analysis of analyte ions, comprising:
   (a) wide-bore capillary having an inlet end and an outlet end, a wide bore zone having a wide bore between said ends, and an opening at each of said ends, at least one of said ends having a restriction zone capable of providing fluid communication between the wide bore and the opening at said end, the restriction zone including a narrow bore extending to the opening and including a transition zone providing gradual change of bore diameter from the wide bore to the narrow bore;
   (b) buffer source to supply buffer to the inlet end of the capillary; and
   (c) power supply for supplying power to drive buffer and analyte ions through the capillary, including electrodes in electrical communication with the inlet end and the outlet end to provide voltage differential between said ends during CE.

2. The apparatus according to claim 1 wherein the wide bore capillary is an integral, unitary piece.

3. The apparatus according to claim 1 wherein the wide bore zone and the restriction zone are individual pieced connected together.

4. The apparatus according to claim 1 wherein each of the ends of the wide bore capillary has a restriction zone.

5. The apparatus according to claim 1 wherein the wide bore has an inside diameter of 75 µm or larger.

6. The apparatus according to claim 1 wherein the wide bore has an inside diameter of 100 µm to 500 µm.

7. The apparatus according to claim 1 wherein the narrow bore has an inside diameter of 20 µm to 75 µm.

8. The apparatus according to claim 1 wherein the narrow bore has an inside diameter of 20 µm to 50 µm.

9. The apparatus according to claim 1 wherein the narrow bore has a length of 10 µm to 1000 µm.

10. The apparatus according to claim 1 wherein the wide bore capillary is of a material selected from the group consisting of fused silica and polymeric material.

11. A method for capillary electrophoresis (CE) analysis of analytes, comprising:
    applying a voltage differential between an inlet end and an outlet of a wide-bore capillary to drive a buffer and analyte ions through the capillary, the wide-bore capillary having an opening at each of said ends and a wide bore, at least one of said ends having a restriction zone capable of providing fluid communication between the wide bore and the opening at said end, the restriction zone including a narrow bore extending to the opening and including a transition zone providing gradual change of bore diameter from the wide bore to the narrow bore, such that the restriction zone substantially prevents siphoning.

12. The method according to claim 11 further comprising the step of providing the wide bore capillary as an integral, unitary piece.

13. The method according to claim 11 further comprising providing the wide bore capillary, wherein the wide bore has an inside diameter of 100 µm to 500 µm.

14. The method according to claim 11 further comprising providing the wide bore capillary, wherein the narrow bore has an inside diameter of 20 µm to 75 µm.

15. The method according to claim 11 further comprising providing the wide bore capillary, wherein the narrow bore has an inside diameter of 20 µm to 50 µm.

16. The method according to claim 11 further comprising providing the wide bore capillary, wherein the narrow bore has a length of 10 µm to 1000 µm.

17. A method of making a wide-bore capillary electrophoresis (CE) apparatus for analysis of analyte ions, comprising:
    (a) making a restricted wide-bore capillary by providing a narrowing of the bore of at least one end portion of a capillary with a wide-bore and an inlet end and an outlet end to form a restriction zone which is capable of allowing fluid communication between the wide bore and the opening at said end, the restriction zone including a narrow bore extending to the opening and a transition zone providing gradual change of bore diameter from the wide bore to the narrow bore;

(b) supplying buffer to the inlet end of the capillary during capillary electrophoresis (CE) by providing a container for containing the buffer; and (c) connecting electrodes to a power supply for supplying power to drive buffer and analyte ions through the capillary during CE, one of said electrodes being positioned in said container to provide electrical communication via the buffer with the inlet end of the capillary during CE, one electrode being positioned proximate said outlet end of the capillary to provide electrical communication thereto during CE such that a voltage differential is applied between said ends of the capillary.

18. The method according to claim 17 further comprising making the wide bore capillary by heating an end portion of the capillary with a wide bore and rotating the capillary with a wide bore to form the restriction zone.

* * * * *